(12) United States Patent
Wholey et al.

(10) Patent No.: US 7,713,227 B2
(45) Date of Patent: May 11, 2010

(54) METHOD AND APPARATUS FOR MEDICAL DEVICE FOR ASPIRATION OF THROMBOEMOBOLIC DEBRIS

(76) Inventors: Michael Wholey, 19407 Straus, San Antonio, TX (US) 78256; Mark H. Wholey, 816 Woodland Ave., Oakmont, PA (US) 15139; Petra Wholey, 19407 Straus, San Antonio, TX (US) 78256

( * ) Notice: Subject to any disclaimer, the term of this patent is extended or adjusted under 35 U.S.C. 154(b) by 2987 days.

(21) Appl. No.: 09/809,468

(22) Filed: Mar. 15, 2001

(65) Prior Publication Data

US 2002/0026212 A1 Feb. 28, 2002

Related U.S. Application Data

(60) Provisional application No. 60/190,513, filed on Mar. 20, 2000.

(51) Int. Cl.
  A61M 37/00 (2006.01)
  A61B 1/267 (2006.01)
  B01D 25/32 (2006.01)
(52) U.S. Cl. .................. 604/6.09; 604/6.01; 604/4.01; 606/200; 210/413
(58) Field of Classification Search ............ 604/4.01, 604/5.01, 6.09, 6.1, 7–10, 19, 43; 210/645, 210/650, 161, 155, 157, 272, 276, 280, 354, 210/359, 383, 398, 500.21, 407, 413; 606/200; 435/290.2–3
See application file for complete search history.

(56) References Cited

U.S. PATENT DOCUMENTS

| | | | |
|---|---|---|---|
| 3,540,431 A | 11/1970 | Mobin-Uddin | |
| 3,692,029 A | 9/1972 | Adair | |
| 3,952,747 A | 4/1976 | Kimmell, Jr. | |
| 4,399,042 A * | 8/1983 | Stannard et al. | 210/791 |
| 4,403,612 A | 9/1983 | Fogarty | |
| 4,406,786 A * | 9/1983 | Hein | 210/223 |
| 4,425,908 A | 1/1984 | Simon | |
| 4,493,711 A | 1/1985 | Chin et al. | |
| 4,496,350 A | 1/1985 | Cosentino | |
| 4,512,762 A | 4/1985 | Spears | |
| 4,564,014 A | 1/1986 | Fogarty et al. | |
| 4,619,246 A | 10/1986 | Molgaard-Nielsen et al. | |
| 4,685,905 A | 8/1987 | Jeanneret nee Aab | |
| 4,723,549 A | 2/1988 | Wholey et al. | |
| 4,755,300 A * | 7/1988 | Fischel et al. | 210/650 |
| 4,790,942 A | 12/1988 | Shmidt et al. | |
| 4,873,978 A | 10/1989 | Ginsburg | |
| 4,876,013 A | 10/1989 | Shmidt et al. | |
| 4,892,518 A | 1/1990 | Cupp et al. | |

(Continued)

FOREIGN PATENT DOCUMENTS

DE 31 07 392 A1 9/1982

(Continued)

*Primary Examiner*—Leslie R Deak
(74) *Attorney, Agent, or Firm*—Alan G. Towner, Esq.; Pietragallo Gordon Alfano Bosick & Raspanti, LLP

(57) ABSTRACT

An apparatus for collecting blood clots, plaque, and other debris in arteries or veins, said apparatus comprising: a filter assembly having a chamber with a paddle assembly and a porous floor disposed therein; and tubes for coupling said filter assembly to an artery and to a vein.

11 Claims, 9 Drawing Sheets

U.S. PATENT DOCUMENTS

| | | |
|---|---|---|
| 4,935,002 A | 6/1990 | Gordon |
| 5,011,488 A | 4/1991 | Ginsburg |
| 5,041,098 A | 8/1991 | Loiterman et al. |
| 5,102,415 A | 4/1992 | Guenther et al. |
| 5,695,511 A | 12/1997 | Cano et al. |
| 5,695,519 A | 12/1997 | Summers et al. |
| 5,704,915 A | 1/1998 | Melsky et al. |
| 5,743,894 A | 4/1998 | Swisher |
| 5,783,085 A | 7/1998 | Fischel |
| 5,814,064 A | 9/1998 | Daniel et al. |
| 5,876,611 A | 3/1999 | Shettigar |
| 5,908,435 A | 6/1999 | Samuels |
| 5,954,745 A | 9/1999 | Gertler et al. |
| 6,042,598 A | 3/2000 | Tsugita et al. |
| 6,059,745 A * | 5/2000 | Gelbfish ............... 604/6.09 |
| 6,416,665 B1 * | 7/2002 | McGrath ............... 210/321.67 |
| 6,645,221 B1 * | 11/2003 | Richter ............... 606/200 |

FOREIGN PATENT DOCUMENTS

DE  89 11 352 U1  1/1990

* cited by examiner

METHOD AND APPARATUS FOR MEDICAL DEVICE FOR ASPIRATION OF THROMBOEMOBOLIC DEBRIS

CROSS REFERENCE TO RELATED APPLICATIONS

This application claims the benefit of U.S. Provisional Patent Application Ser. No. 60/190,513, filed Mar. 20, 2000.

BACKGROUND OF INVENTION

1. Field of Invention

This invention relates to an apparatus and method for collecting blood clots, pieces of plaque and other material that may be accidentally dislodged during interventional procedures in the human vasculature such as arterial and venous angioplasty and stent placement. The invention utilizes a chamber that collects the blood from one sheath or catheter through an aspirating force where the blood can be filtered with removal of thromboembolic debris. The blood can then be recirculated back into the bloodstream through a second access.

2. Background Information

It is common practice today to open occluded (i.e. blocked) or stenotic (i.e. narrowed) blood vessels by inserting a guidewire and then a catheter carrying a balloon shaped distal end and inflating the balloon, which exerts radial force, to press the stenosis outward against the wall of the vessel. This procedure is called balloon angioplasty. Frequently, an implantable metallic stent will be used additionally to provide greater radial strength and longer-term patency.

In order to help deliver the balloon catheters and the stent devices, special guiding catheters or sheaths are used. These guide catheters or sheaths are placed away (or upstream) from the targeted lesion. A guidewire will be advanced past the lesion, allowing the subsequent balloon catheters and stents to be advanced through the guiding catheter or sheath to the target lesion.

During balloon angioplasty and stent placement of the stenotic lesion, there is the risk of dislodging fragments of plaque, thrombus (blood clots) or other material. If the lesion involves arterial circulation, then the particles could flow into smaller vessels in the brain, other organs or extremities resulting in disastrous complications. Likewise, if the lesions involve the venous circulation, then the thromboemboli could flow into the heart and lung possibly resulting in the demise of the patient.

It is the primary purpose of the present invention to provide such a protection. The device can be easily and remotely attached to catheters and sheaths ends. By initiating the device, slow and continuous aspiration will started. Blood will be drawn from the one vessel, filtered and then recirculated into the other vessel. This will allow effective trapping and removal of thromboembolic material.

The device could be attached to the proximal end of special guiding catheters that have a soft occluding balloon used to occlude flow into the vessel. Distal protection could also be provided by the insertion of a small balloon catheter in important branch vessels or past the lesion. Likewise, it can be attached to regular sheath or guiding catheter and provide needed aspiration during key parts of the case.

Benefits of the current invention include low speed rotating paddles or wheels which minimize trauma to individual blood cells which otherwise leads to hemolysis and potential problems such as rhabdomyolysis. Also, since it is a closed loop, there will be little if any blood loss.

The invention will have tremendous benefit in such procedures as carotid artery angioplasty and stent placement, where the incoming loop is attached to the guiding catheter or sheath in the artery and the outgoing system is attached to the venous sheath.

The invention will also have benefit in any procedure with the risk of thromboembolic debris such as other peripheral interventions as well as venous cases.

DESCRIPTION OF PRIOR ART

There have been various devices and equipment to deal with stenotic lesions. As described, angioplasty and stents have been used to radially expand the lesion into the wall of the vessel. But these instruments can accidentally dislodge plaque and thrombus. Atherectomy devices are used to cut the plaque but have poor clinical results in actually treating the lesion and do not effectively trap thromboemboli.

Various patents have recently addressed the subject with the use of balloons or straining devices. However, their designs do not effectively trap particles or are too traumatic in crossing high grade stenoses. This invention provides these capabilities in addition to being attached simply to existing conventional guide catheters and sheaths.

BRIEF DESCRIPTION OF THE DRAWINGS

A full understanding of the invention can be gained from the following description when read in conjunction with accompanying drawings in which.

DESCRIPTION OF PREFERRED EMBODIMENTS

Figure 1:
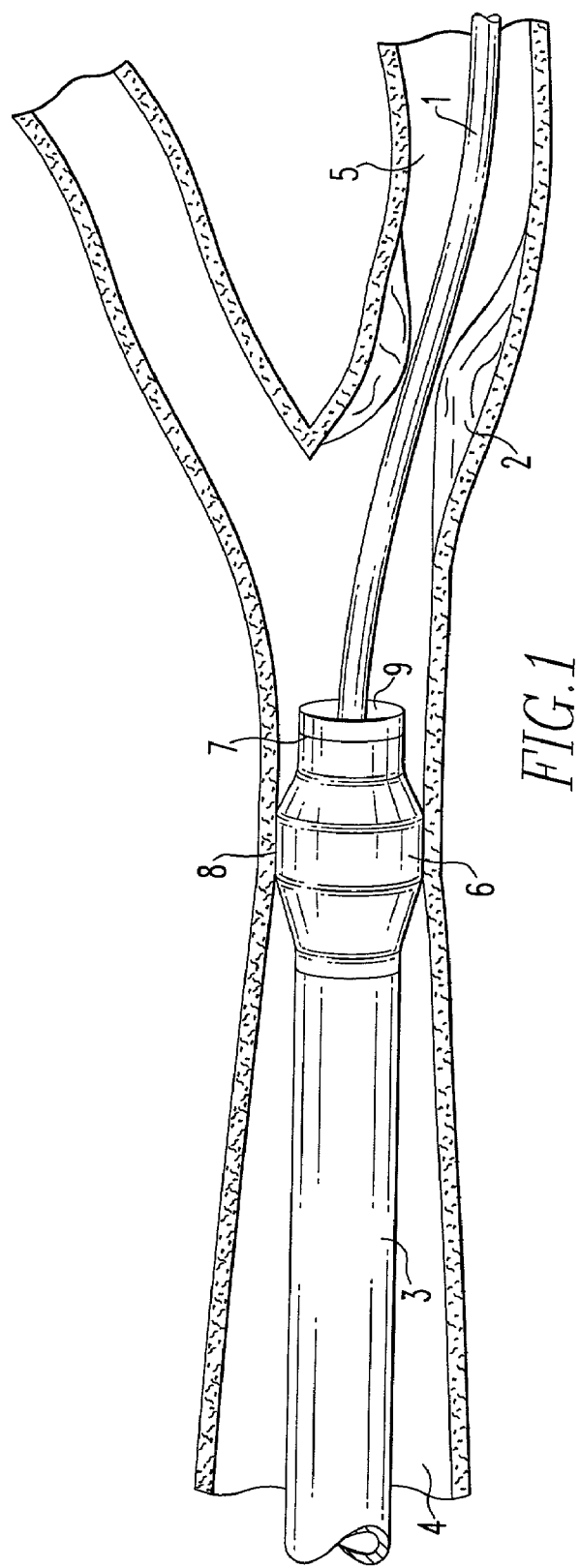
FIG. 1 is a longitudinal cross sectional view through a vessel such as a carotid artery showing the common carotid artery and the branches of the internal and external carotid arteries. Shown is the end of a guide catheter with a balloon near the distal tip. The inflated balloon is opposed to the vessel wall, helping to prevent thromboemboli from being sent downstream and into the cranial circulation. Also shown is a guidewire crossing the lesion. Over this guidewire, balloon catheters and devices to deliver and deploy the stent will be used.
Figure 2:
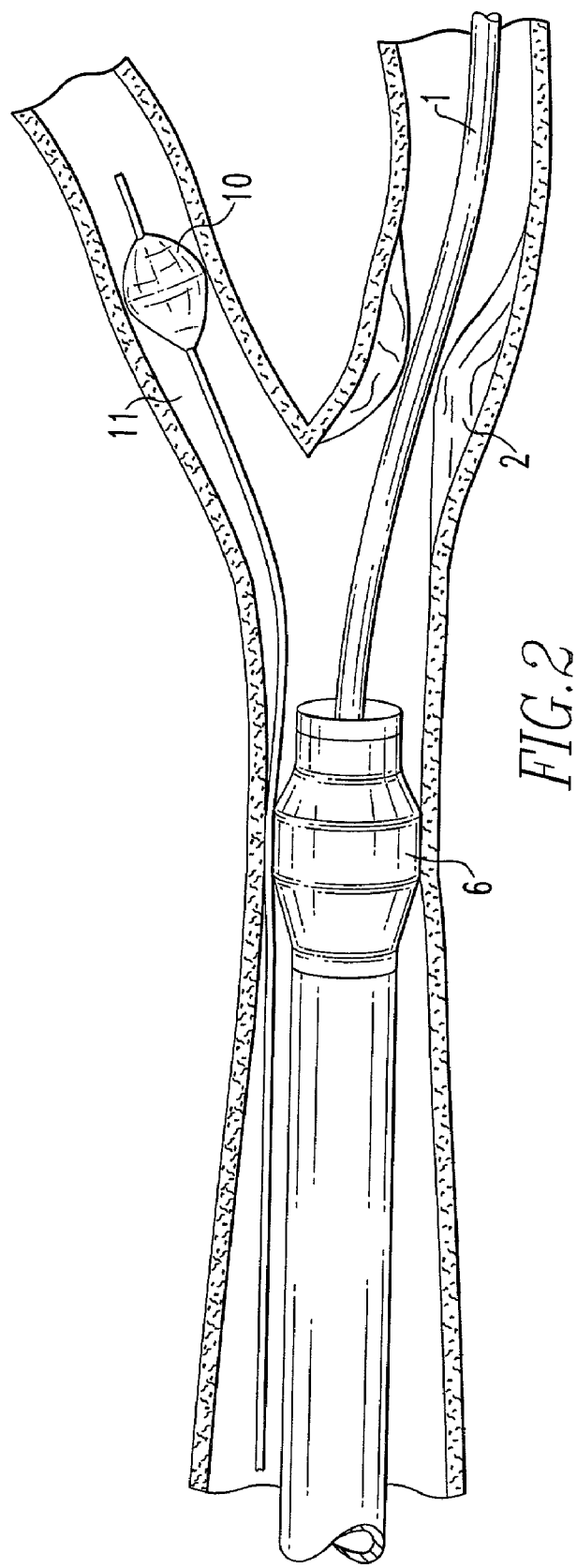
FIG. 2 is a longitudinal cross sectional view as shown in FIG. 1 with the addition of second balloon catheter advanced and placed in the external carotid artery.
Figure 3:
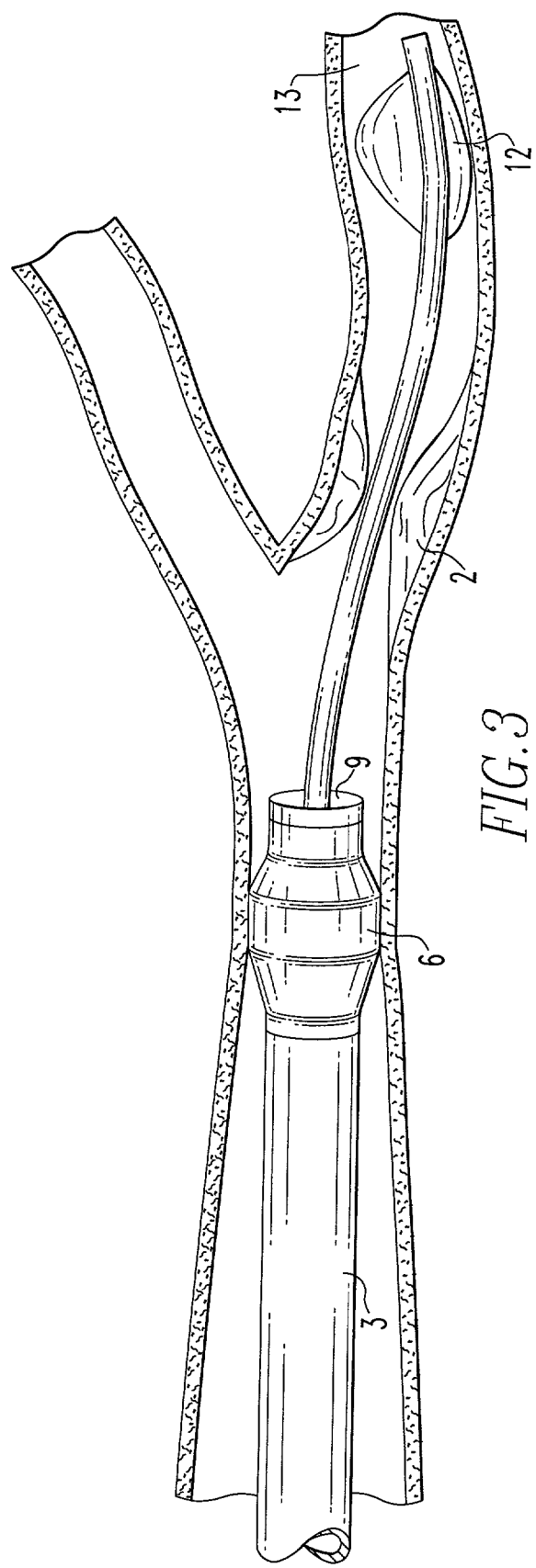
FIG. 3 is a longitudinal cross sectional view as shown in FIG. 1 with the addition of second balloon catheter advanced and placed in the internal carotid artery past the lesion in the artery.
Figure 4:
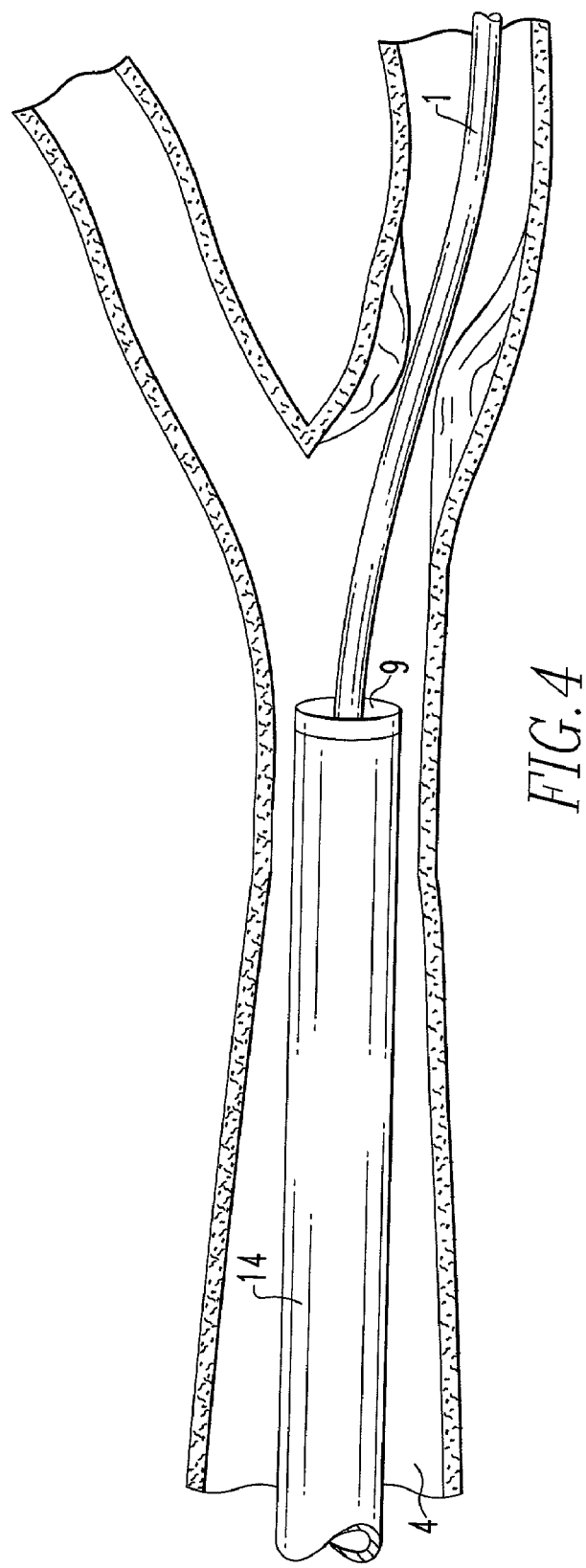
FIG. 4 is a longitudinal cross sectional view as shown in FIG. 1 without the distal balloon segment.
Figure 5:
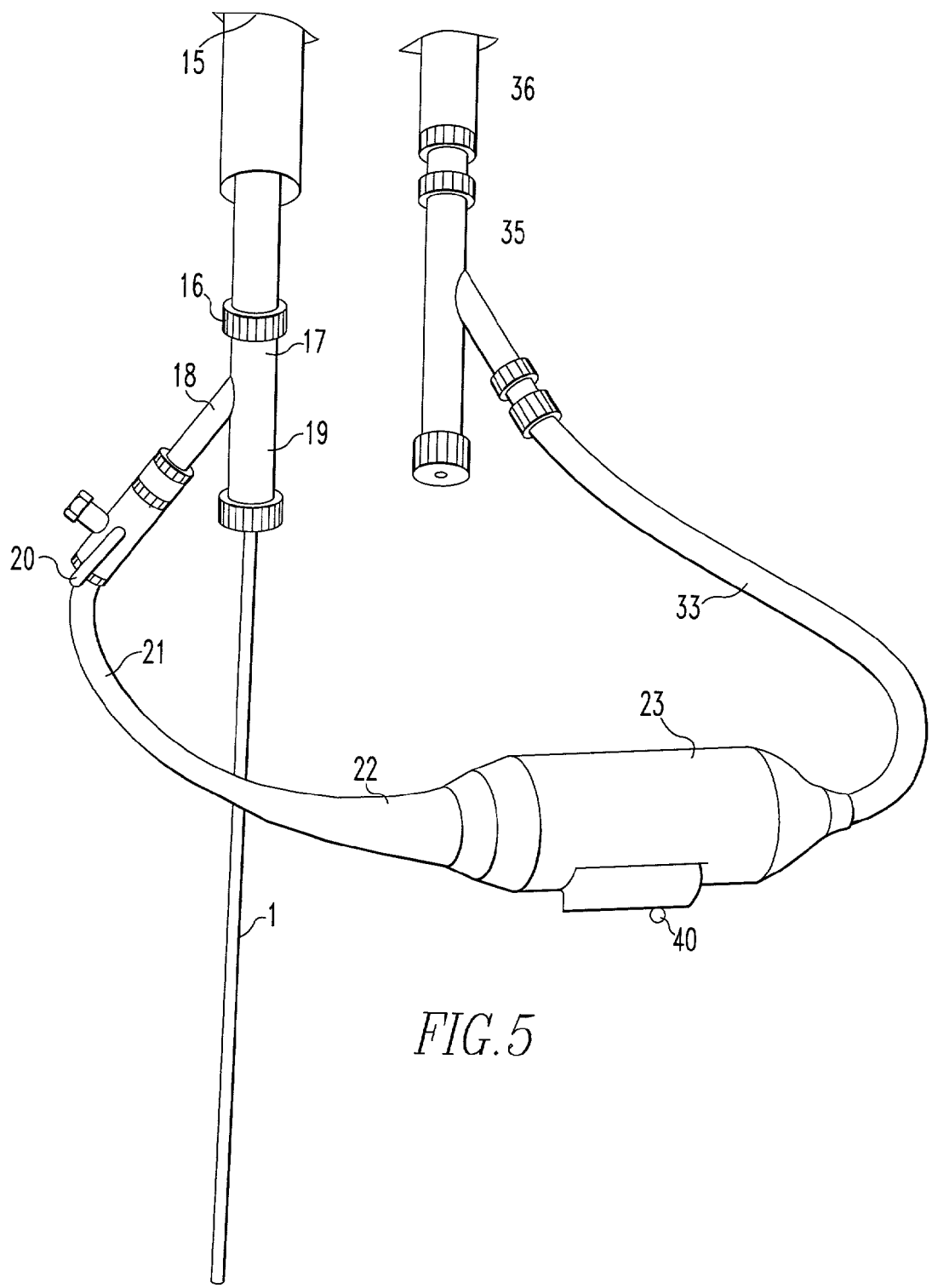
FIG. 5 is a top-down view of the device attached to "Y-adaptors" which are attached to the proximal ends of two guide catheters and/or vascular sheathes. The guide catheters and sheaths are inserted via the groin into the common femoral artery and vein.
Figure 6:
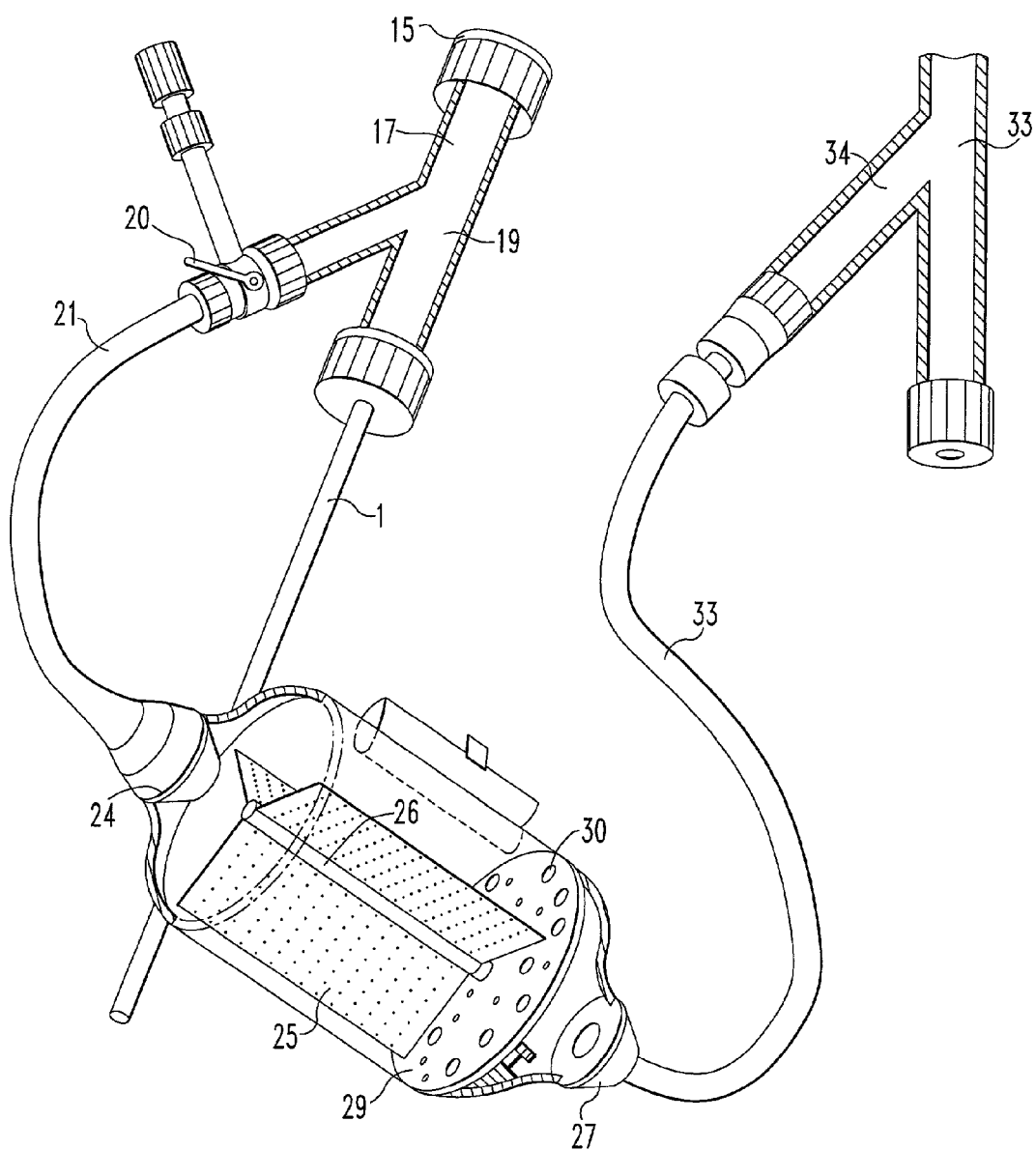
FIG. 6 is a top-down cross sectional view of the aspiration device with the ends attached through "Y-adaptors" which are connected to arterial and venous sheaths or guide catheters.
Figure 7:
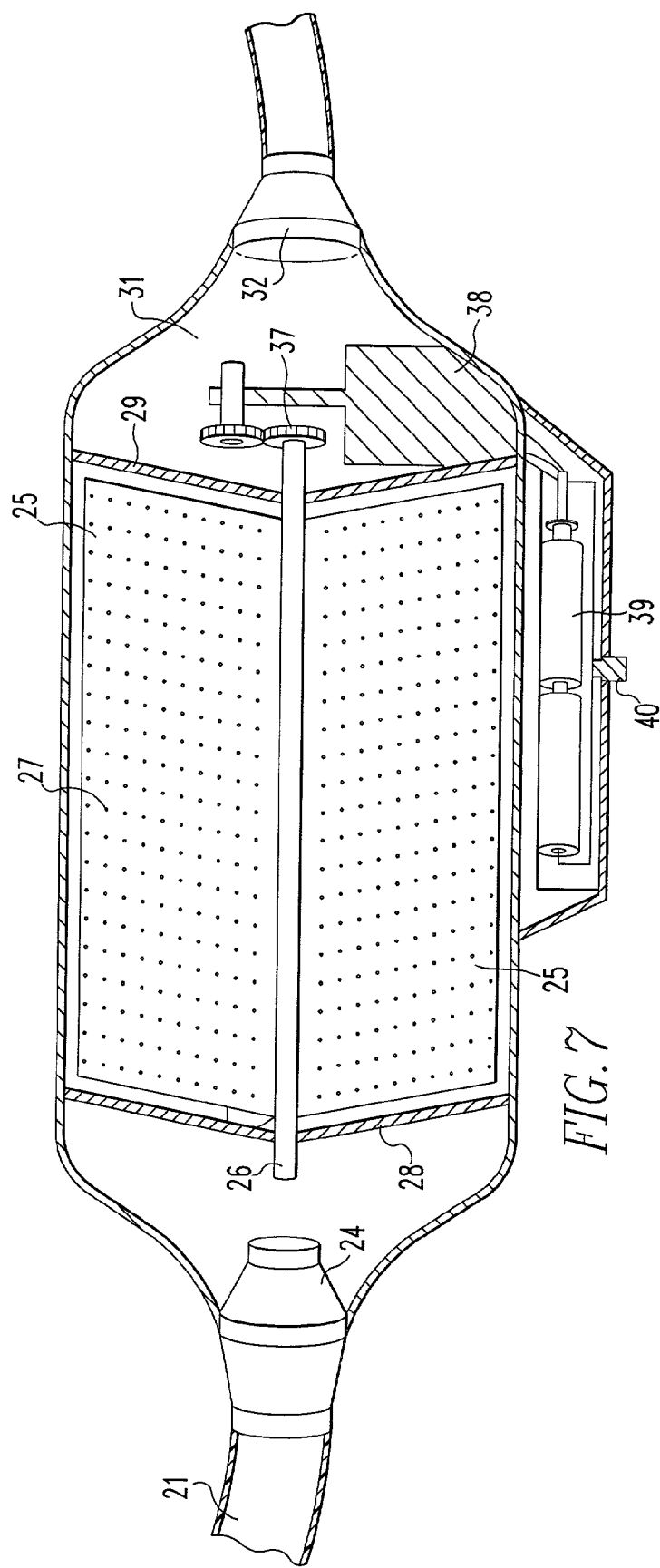
FIG. 7 is a cross-sectional lateral view of the aspiration device.

As shown in FIGS. 1-7, after a guidewire (1) is inserted into a blood vessel narrowed by a stenosis (2), a guiding catheter or long vascular sheath (3) is coaxially advanced proximal to the targeted lesion (2). In the present case, the distal end of the guiding catheter is located in the common carotid artery (4) and the targeted lesion (2) is located in the origin of the internal carotid artery (5). In this case, a special guiding catheter (3) is shown with a soft, expansible balloon (6) located near the distal tip (7). When the balloon (6) is inflated, the balloon will oppose against the vessel wall (8). This guiding catheter will have the balloon inflated during key parts of the case helping to prevent distal emboli from flowing downstream. The inflated balloon will also help provide increased aspiration force. When aspiration is begun, blood and thromboembolic debris from the treated lesion (2) will be drawn into through the main lumen (9) of the guiding catheter or long vascular sheath (3).

Minor modifications to the procedure would include the additional passage of a small balloon catheter (10) into a branch artery, such as the external carotid artery (11) in this case. Likewise, a separate, coaxial balloon guidewire/catheter (12) could be used through the guiding catheter (3) and when inflated, complete blockage will be obtained both proximal and distal to the lesion (13). Finally, aspiration through main lumen (9) could be obtained through conventional guiding catheters and vascular sheaths (14) without the occluding balloon segment.

Aspirated blood and thromboembolic debris is drawn through the main lumen (9), the proximal end of the guiding catheter (15), which exits the patient, and through and the luer lock insertions (16). A "Y-adaptor" (17) attaches to the main lumen (9) through this luer lock (16). The "Y-adaptor" (17) is composed of a sidearm port (18) and a main channel (19), through which runs guidewires and other coaxial systems. The sidearm (18) of the "Y-adaptor" (17) is attached to a three-way stopcock (20). The inflow tubing (21) of the present invention is attached through this three-way stopcock (20).

The inflow tubing (21) inserts into the proximal end (22) of the invention chamber (23). There is a one-way valve (24) to prevent backflow of blood and thromboembolic debris. Two-to-four paddles (25) rotate within the invention chamber (23) upon a central axis (26). There are micropores (27) within the paddles (25) to prevent hemolysis. The blood and thromboembolic debris first pass through an anterior wall (28), through the paddle section (25) and then pass through a posterior floor (29) at the base of the chamber. The posterior floor (29) has pores (30) of varying size to serve as sieve, allowing blood to pass to the distal end (31) of the device, while capturing thromboembolic debris. Blood will pass through the distal one-way valve (32) and into the outflow tubing (33) where it is inserted on to the sidearm (34) of a "Y-adaptor" (35) which is attached to the venous sheath (36). Blood is then returned back into the circulation.

The central axis (26) rotates through a series of flywheels (37) which are rotated though a small engine (38). The engine (38) is powered by batteries or electrical source (39) located on the outside of the chamber. There is a small switch (40) to operate the device.

Figure 8:
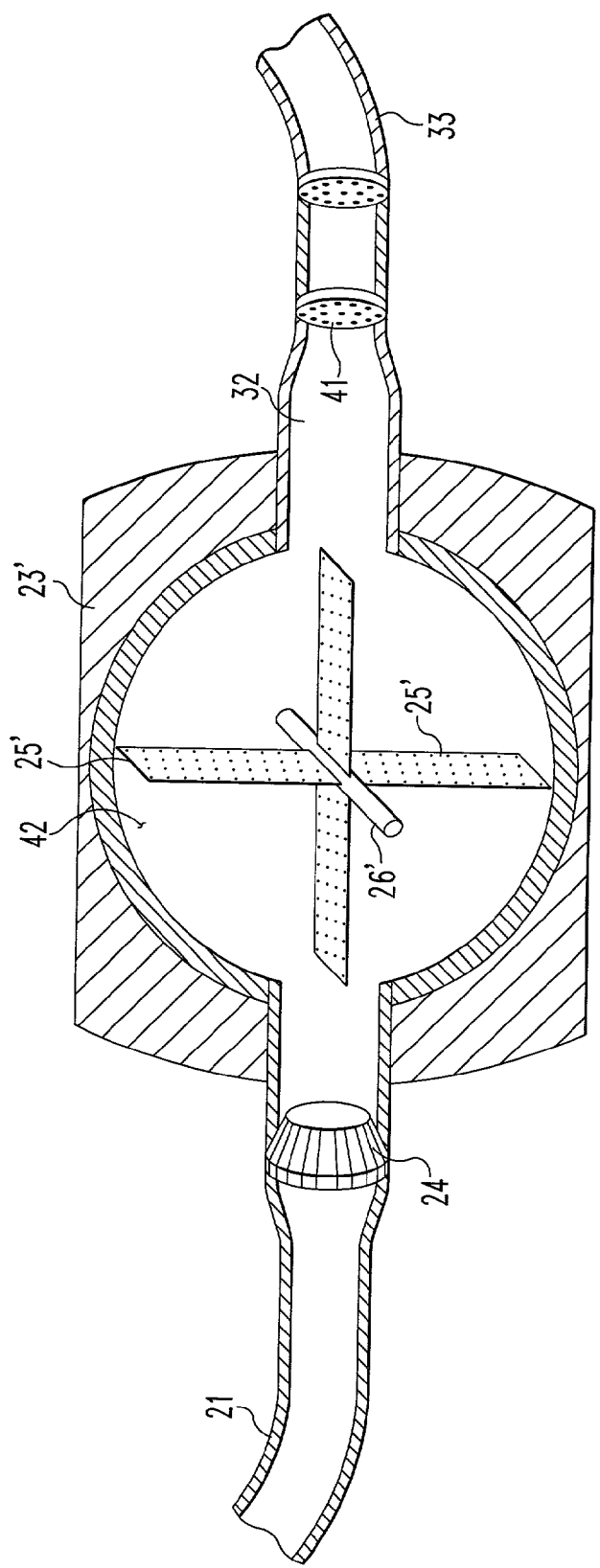
FIG. 8 is a cross-sectional side view of an alternate embodiment.
Figure 9:
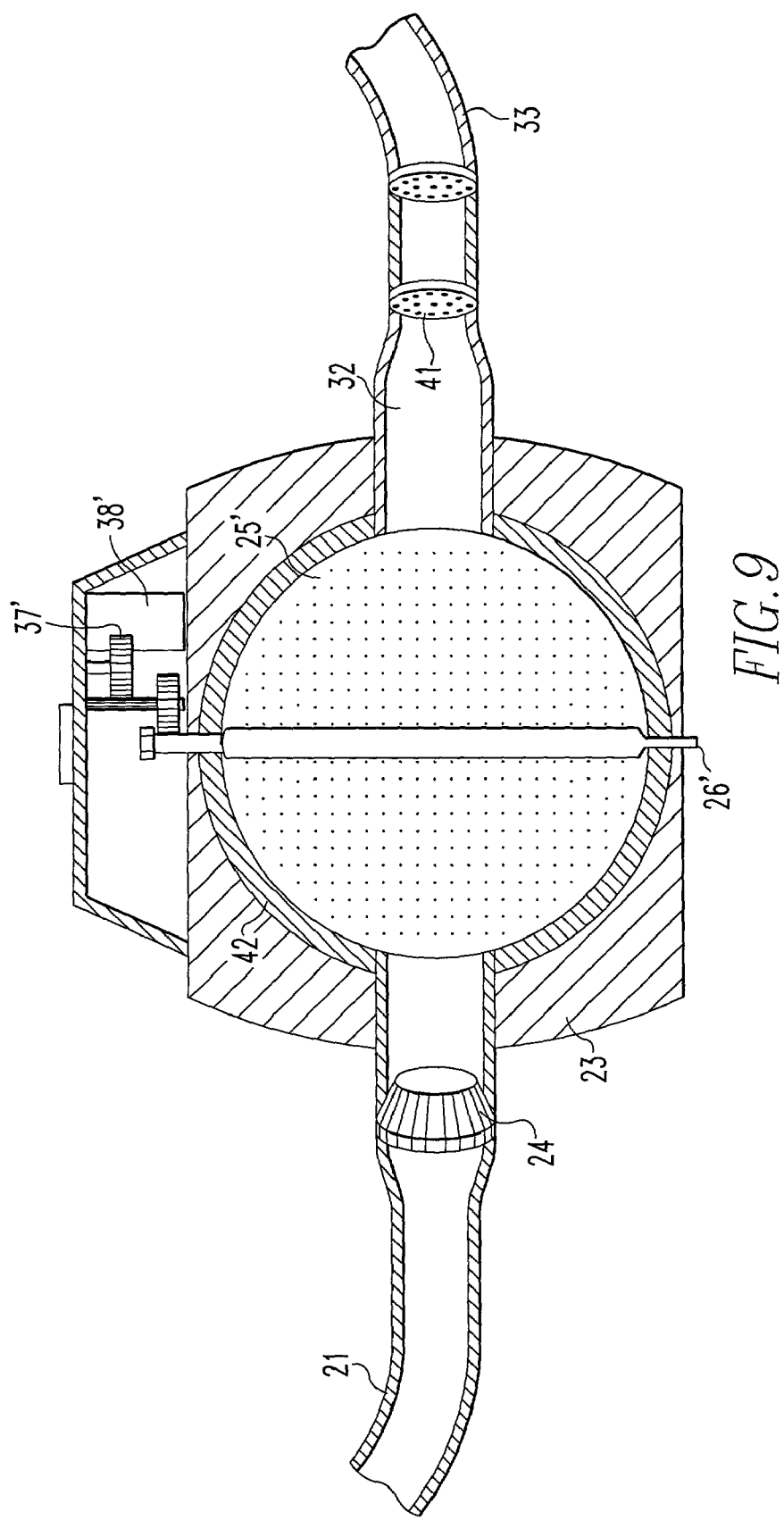
FIG. 9 is a cross-sectional top view of the alternate embodiment.

An alternate embodiment of the invention is shown in FIGS. 8 and 9. In this embodiment, the chamber 23' includes a spherical inner chamber 42. Within spherical chamber 42 are semicircular paddles 25'. The paddles 25' rotate on an axis 26' which is disposed generally perpendicular to the axis of the elongated chamber 23. The axis 26' extends beyond the chamber 23. As such, the fly wheels 37' and engine 38' are disposed outside of the chamber. An additional filter 41 may be disposed in the outflow tubing 33.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. An apparatus for collecting blood clots, plaque, and other debris in arteries or veins, said apparatus comprising:
   a filter assembly forming an elongated chamber;
   a paddle assembly disposed in said chamber comprising at least one paddle having front and rear exterior surfaces defining a thickness of the paddle and pores extending through the thickness of the paddle from the front surface to the rear surface of the paddle;
   a porous floor disposed within and extending across said chamber; and
   a means for coupling said filter assembly to an artery and/or to a vein.

2. The apparatus of claim 1, wherein:
   said paddle assembly includes a rotatable axis and at least two of the paddles extend therefrom; and
   said pores in said paddles being micro pores.

3. The apparatus of claim 2, wherein said axis extends at a generally perpendicular angle from said porous floor and generally along the axis of said chamber.

4. The apparatus of claim 3, wherein:
   said chamber is generally cylindrical having a proximal end and a distal end; and
   said porous floor is disposed adjacent to said distal end.

5. The apparatus of claim 4, wherein said porous floor is structured to allow blood to flow therethrough and to capture debris.

6. The apparatus of claim 5, wherein:
   said filter assembly includes an anterior wall;
   said anterior wall having a one-way valve structured to allow blood to flow into said chamber; and
   said distal end includes a one-way valve structured to allow blood to flow out of said chamber.

7. The apparatus of claim 6, wherein:
   said filter assembly includes an engine having a shaft and structured to produce rotation in said shaft; and
   said shaft coupled to said axis whereby said axis is rotated.

8. The apparatus of claim 7, wherein said means for coupling said filter to an artery and/or a vein is in fluid communication with said anterior wall one-way valve and said distal end one-way valve.

9. The apparatus of claim 8, wherein said means for coupling said filter to an artery and/or a vein includes:
   a guiding catheter in fluid communication with said artery;
   a catheter Y-adaptor;
   a three-way stopcock;
   an inflow tube; and
   said guiding catheter, catheter Y-adaptor, three-way stopcock and inflow tube structured to be in fluid communication with each other and said anterior wall one-way valve whereby fluid within said guiding catheter may travel through said Y-adaptor, three-way stopcock and inflow tube into said filter assembly.

10. The apparatus of claim 9, wherein said means for coupling said filter to an artery and/or a vein includes:
an outflow tube in fluid communication with said distal and one-way valve;
a venous Y-adaptor;
a venous sheath in fluid communication with said vein; and
said outflow tube, venous Y-adaptor, and venous sheath structured to be in fluid communication with each other whereby fluid in said filter assembly is returned to said vein.

11. The apparatus of claim 10, wherein:
said guiding catheter has a distal end structured to be inserted in said artery; and
said distal end having an integral balloon.

* * * * *

UNITED STATES PATENT AND TRADEMARK OFFICE
CERTIFICATE OF CORRECTION

PATENT NO. : 7,713,227 B2  
APPLICATION NO. : 09/809468  
DATED : May 11, 2010  
INVENTOR(S) : Michael Wholey, Mark H. Wholey and Petra Wholey Page 1 of 1

It is certified that error appears in the above-identified patent and that said Letters Patent is hereby corrected as shown below:

Title Page

Item (54) Title, and col. 1, line 3
"Thromboemobolic" should be "Thromboembolic"

Signed and Sealed this
Twentieth Day of December, 2011

David J. Kappos
*Director of the United States Patent and Trademark Office*